United States Patent [19]

Wohlstein et al.

[11] Patent Number: 5,691,701
[45] Date of Patent: *Nov. 25, 1997

[54] FLUID OR VAPOR DIAGNOSTIC DEVICE

[75] Inventors: Scott D. Wohlstein, Convent Station, N.J.; Emil W. Ciurczak, Laurel, Md.

[73] Assignee: SD Laboratories, Inc., Franklin, Pa.

[ * ] Notice: The term of this patent shall not extend beyond the expiration date of Pat. No. 5,296,843.

[21] Appl. No.: 216,557

[22] Filed: Mar. 22, 1994

Related U.S. Application Data

[63] Continuation-in-part of Ser. No. 677,643, Mar. 28, 1991, Pat. No. 5,296,843.

[51] Int. Cl.$^6$ .................................................. G08B 21/00
[52] U.S. Cl. ..................... 340/603; 340/438; 250/573; 250/575; 356/70; 356/320; 356/436
[58] Field of Search ........................ 340/603, 438, 340/619, 632; 250/573, 575; 356/70, 319, 320, 436

[56] References Cited

U.S. PATENT DOCUMENTS

| | | | |
|---|---|---|---|
| 3,927,944 | 12/1975 | Iwahashi et al. | 356/97 |
| 4,227,811 | 10/1980 | Tohyama et al. | 356/319 |
| 4,300,689 | 11/1981 | Franklin et al. | 356/418 |
| 4,350,441 | 9/1982 | Wicnienski | 356/320 |
| 4,534,651 | 8/1985 | Minikane | 356/440 |
| 4,570,069 | 2/1986 | Gager | 356/70 |
| 4,649,711 | 3/1987 | Sibley et al. | 340/631 |
| 4,699,509 | 10/1987 | Kamiya et al. | 356/70 |
| 4,755,048 | 7/1988 | Kaufman | 356/407 |
| 4,911,549 | 3/1990 | Karkar | 356/320 |
| 4,929,847 | 5/1990 | Yamazoe et al. | 250/573 |
| 5,296,843 | 3/1994 | Wohlstein et al. | 340/438 |

*Primary Examiner*—Jeffery Hofsass
*Assistant Examiner*—Benjamin C. Lee
*Attorney, Agent, or Firm*—Curtis D. Kinghorn

[57] ABSTRACT

A device is provided which passes light of preselected wavelengths through a fluid, gas or vapor to be tested. The light is detected after it has passed through the fluid, gas or vapor. Upon detection, a voltage is created which is proportional in amplitude to the detected light strength for each wavelength of light. These voltages are compared to produce a ratio which represents the condition of the fluid, gas or vapor which is tested or the presence of an analyte of interest. When the ratio is outside of preselected boundaries, control signals are generated which may trigger alarms or otherwise respond to the condition. In a preferred embodiment of the invention, the presence of carbon gases such as carbon monoxide and carbon dioxide is detected in gases or vapors.

16 Claims, 3 Drawing Sheets

FLUID OR VAPOR DIAGNOSTIC DEVICE

This application is a continuation-in-part of application Ser. No. 07/677,643, filed Mar. 28, 1991 now U.S. Pat. No. 5,296,843.

FIELD OF THE INVENTION

The invention relates to a fluid or vapor diagnostic device and more particularly to a device which non-destructively determines the quality of a fluid or vapor tested by passing light of different wavelengths through the fluid or vapor and then comparing the ratio of the resulting detected light strengths to a predetermined ratio indicating whether the operating parameters of the fluid or vapor are within acceptable limits.

BACKGROUND OF THE INVENTION

Throughout this description, reference to "fluids" refers to both fluids, gases and vapors unless stated otherwise. It has been found that when many fluids are exposed to a variety of environmental conditions, their physical properties change. These changes occur primarily in two areas. The chemical composition of the fluid itself may be changed through the application of heat, pressure, chemical reactions with other fluids, or air-oxidation. In addition, the fluid may be contaminated by other fluids, contaminants or particulate matter from other sources, which, although not chemically combining with the fluid, affects the fluid's ability to function as it was intended, which function is best accomplished by a pure fluid.

Exemplary of such a fluid susceptible to both of these changes is lubricating motor oil used in an internal combustion engine. A pure motor oil is ideally suited for providing lubrication within the internal combustion engine. However, due to the high temperature necessarily present in such engines, breakdown of the molecular structure of the motor oil takes place with resulting loss of lubricating ability. The remnants of the broken down motor oil molecules remain in the motor oil as contaminants. In addition, other contaminants such as carbon deposits and fine metal particles which result from the operation of the engine are also introduced into the motor oil thereby contaminating it. Other contaminants are introduced into the motor oil such as water or anti-freeze from the engine cooling system. Dust particles, introduced into the engine with the air through the carburization system, are blown past compression and oil rings into the engine crank case from the combustion chamber during the compression stroke of the pistons.

Given time, the breakdown of pure motor oil and the introduction of contaminants into the motor oil renders the motor oil unable to effectively perform its job of lubricating the engine parts. When this occurs, the used motor oil should be replaced with new motor oil. The amount of time it takes for motor oil to reach this condition depends on a variety of factors including the strain put on the engine, the adequacy of cooling measures related to the engine, and external environment of the engine during operation.

Many fluids have additives added to them to enhance their inherent capabilities. These additives result in variant chemical and light absorbing properties. Examples of such chemicals are the various types of fuel enhancers used in the automotive fuel industry. For example, the introduction of ethanol, a common additive in many fuels, radically changes in a predictable way the overall light absorption properties of the resultant ethanol gasoline mixture.

Further, it is often desirable to detect the presence of a particular substance in a fluid, gas or vapor. For example, in devices that emit or detect infrared radiation, it is desirable to detect the presence gases that affect the device's ability to accurately detect or emit the infrared radiation. Carbon based gases such as carbon monoxide or carbon dioxide are examples of gases that absorb infrared radiation. Therefore, it is often desirable to detect the presence of these gases.

The invention was designed to detect both when a fluid, either by breakdown or by contamination, has moved outside of an acceptable range of operating parameters, and also when the presence of certain additives or other fluids, gases or vapors are present in the tested fluid.

SUMMARY OF THE INVENTION

In researching the above mentioned two problems, it was discovered that the light absorbing properties of a fluid is altered by the breakdown of the fluid itself, or by the introduction of contaminants or additives into the fluid. It was also discovered that breakdown or contamination of the fluid affects the light absorbing characteristics of the fluid by different amounts for different wavelengths of light. In particular, it was found that a ratio established by passing light of various wavelengths through the fluid to be tested and then detecting and comparing the strength of the light after passing through the fluid indicates the condition of the fluid related to the above mentioned detrimental characteristics or indicates the presence of an additive. In particular, it was found that when the ratio for the preselected wavelengths reaches a certain ratio, the fluid is no longer within acceptable standards set for the fluid or contains certain amount of an identifiable additive.

In the case where the fluid is changing due to use or contamination, because the change in fluid takes place within the environment where the fluid is found and because change in the fluid is a continuous process, the fluid should be tested continuously while it is being used in order to immediately detect detrimental changes. In this context, it is preferable to non-destructively, continuously test the fluid so that the testing process itself does not contribute to the breakdown and contamination problems of the fluid. Therefore, the light of various wavelengths should be introduced to the fluid in such a way that it can continuously and non-destructively interact with the fluid while helping to determine the condition of the fluid.

Light of preselected wavelengths is passed through a fluid to be tested. The light is detected after passing through the fluid. Thereafter, a voltage is created for each wavelength of light, proportional in amplitude to the detected light strength of each wavelength. These proportional voltages are compared to produce a ratio which represents the condition of the fluid. When the ratio is outside a preset acceptable limit, control signals, which may trigger alarms or other warning devices, are triggered.

The light of the selected wavelengths is created preferable by appropriate photodiodes. The light is introduced into the fluid to be tested by transmitting the light of the various frequencies through respective fiber optic cables into a reservoir of the fluid. There the light is emitted across a gap through which the fluid may travel. The emitted light is then received through a corresponding fiber optic cable on the other side of the gap. The received light is transmitted through a fiber optic cable out of the reservoir where its strength may be determined.

The signal strength of the light received across the gap is determined by having the light impinge on a detector which produces a voltage output proportional to the impinging light strength. The resulting electronic analog signal may be processed to amplify it and filter noise present with the signal. Thereafter, the electronic signals corresponding to the detected light strengths from the different wavelengths are electronically combined to from a ratio. This ratio has been found to represent the quality of the fluid that is being tested.

The ratio is analyzed to determine whether it lies within preselected boundaries representing acceptable qualities of the fluid. If the ratio is found to be outside of these boundaries, control signals are generated to draw attention to the unacceptable quality of the fluid.

In the preferred embodiment, a probe containing the light emitting and receiving fibers, as well as the gap between them, is mounted in the wall of a reservoir of a fluid to be tested. The light creating devices, the light detectors, ratio determining and analyzing circuitry, control signal generator circuitry, and alarm means are all located outside the fluid reservoir. However, it is possible to have both the probe containing the light emitting and receiving fibers, as well as the gap between them, and the light creating devices, the light detectors, ratio determining and analyzing circuitry, control signal generator circuitry, and alarm means all located inside the fluid reservoir. In this embodiment, control signals are sent out of the reservoir by appropriate means.

In an alternate embodiment, a handheld unit having a probe comprising respective input and output fiber optics separated by a gap is provided. The probe may be immersed into a selected fluid for testing. In this embodiment, the operation of the device is exactly the same as that described above except that the gap and fiber optic cords are not continuously present within the fluid reservoir to be tested, but are instead inserted into the fluid at the discretion of the user.

It is an object of the invention to provide a device for non-destructive testing of fluids in real time in the environment where the fluids are found under work conditions.

It is another object of the invention to provide a device that detects additives or contaminants to a fluid.

It is another object of the invention to provide a device which non-destructively tests the conditions of the fluid by determining the amount of light transmitted through the fluid.

It is another object of the invention to provide a device which non-destructively analyzes the composition of the fluid to be tested by comparing the ratios of light of varying wave lengths after it has been passed through the fluid to be tested.

It is a further object of the invention to alert the operator when the ratio of the strength of light of varying wavelengths after being passed through the fluid to be tested indicates that the operating parameters of the fluid are outside a preselected range of values.

It is another object of the invention to provide a device which may be mounted in contact with the fluid to be tested to continuously monitor the condition of the fluid.

It is yet another objective of the invention to provide a device which is inexpensive to manufacture and simple to build.

These and other objectives of the invention will become clear from the foregoing and from the following Detailed Description of the invention.

DETAILED DESCRIPTION OF THE PREFERRED EMBODIMENT

Figure 1:
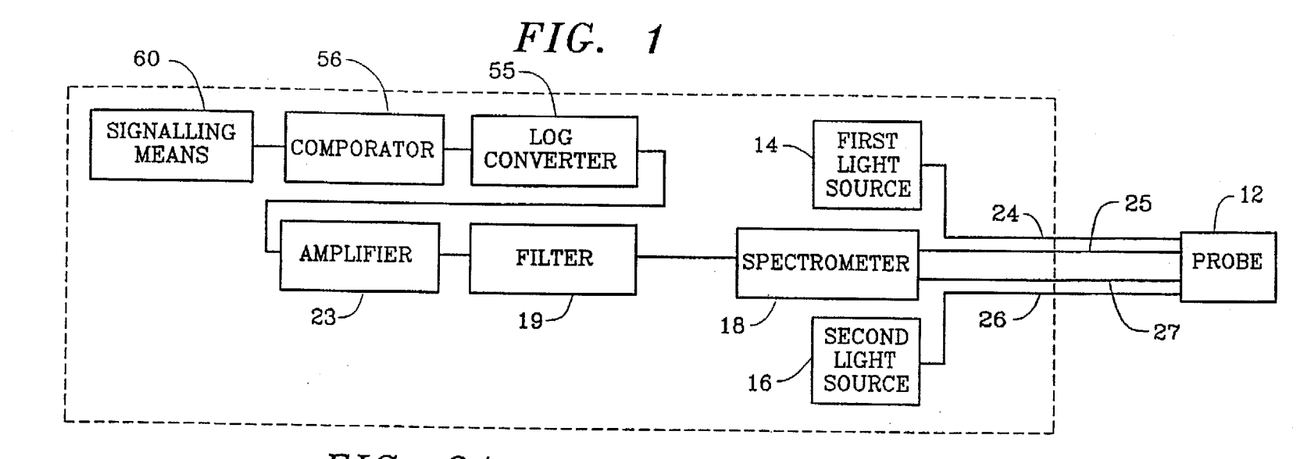
FIG. 1 is a block diagram of the invention.

FIG. 1 shows a block diagram of the invention generally labeled 10. A probe 12 (FIG. 2A, B) is placed in contact with the fluid or vapor to be tested. First and second light sources 14, 16, (FIG. 3) respectively, each provide light of a preselected wavelength to probe 12 through first and second input cables 24, 26 respectively. Preferably, first and second light source 14, 16 are photo-diodes while first and second input cable 24, 26 are fiber optic cables.

In the preferred embodiment the photo-diodes are chosen to have specific emission frequencies for the particular fluid to be analyzed. These preselected wavelengths have been experimentally determined to yield optimum results in determining the quality of the fluid that is tested. Experience has shown that for most fluids, the wavelength of light used ranges from 0.4 micrometers, which is in the visible range, to 5 micrometers which is in the midinfrared range.

In analyzing ordinary motor oil, for example, it has been found that wavelengths of 450 nm and 550 nm yield the most accurate determination of the quality of the motor oil. Alternately, in analyzing JP-10 jet fuel vapors, the fuel used in missile and rocket propulsion, the wavelength of 1500 nm has been found to be particularly effective.

Although photo diodes are the preferred light source 14, 16 for the invention, any other source of light which is able to produce selected wavelengths such as standard LEDs, SRLEDs, or laser diodes are within the scope of the invention. Additionally, lasers at the preselected wavelengths, monochromatic incandescent light sources, or filtered light which produces light at the preselected wavelengths may also be used. These examples are merely exemplary and not intended to be limiting. The important thing is that light, including possibly modulated light, of preselected wavelengths is made available. The preselected wavelengths may be either fixed wavelengths or preselected bands of wavelengths which may be scanned.

Figure 2A:
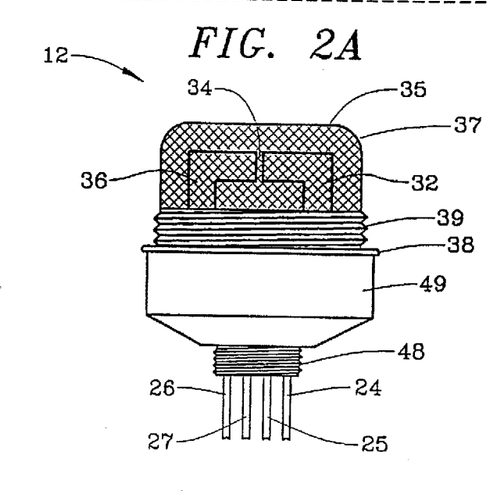
FIG. 2A is a side view of the probe.

First and second input cables 24, 26 are attached on their opposite ends to probe 12 as shown in detail in FIG. 2A. Cables 24, 26 are fiber optic cables. As can be seen, the first and second input cables 24, 26, enter probe 12 through a connector 48. Connector 48 is in turn attached to bulk head 49. The fiber optic cables of first and second input cables 24 and 26 extend through connector 48 and bulk head 49 and exit bulk head 49 through first and second emission fibers 36, 46, respectively which are also fiber optic cables.

Also extending out of the end of bulk head 49 are first and second detection fibers 32, 42 also comprised of fiber optic cables. In the preferred embodiment, each light source has its own fiber optic cable carrying that light to and from the fluid reservoir. A first and second gap 34, 44 separates the emission fibers 36, 46 and detection fibers 32, 42 respectively. First and second gaps 34, 44 allow the fluid or vapor of interest to move between the respective emission fibers 36, 46 and detection fibers 32, 42. Depending on the fluid to be analyzed, the gap 34, 44 between respective emission and detection fibers 36, 32 and 46, 42 may be quite small, possibly even being as small as a millimeter. Table 1 shows the length of the gap 34, 44 found to be most effective in analyzing the corresponding fluid or vapor with the respective wavelength of light. Also shown is the type of analysis possible and whether the analysis is qualitative or quantitative.

TABLE 1

| FLUID/VAPOR | WAVELENGTH RANGE | GAP LENGTH | TYPE OF ANALYSIS |
| --- | --- | --- | --- |
| Oil base lubricant (fluid) | 400–700 nm | 1–20 mm | Qualitative |
| Hydraulic Oil (fluid) | 400–700 nm | 1–20 mm | Qualitative |
| Brake fluid (fluid) | 400–700 nm | 1–20 mm | Qualitative |
| Transmission fluid (fluid) | 400–700 nm | 1–20 mm | Qualitative |
| Coolant or Radiator fluid (fluid) | 400–700 nm | 1–20 mm | Qualitative |
| Organic, Carbon based Fuel (Example-gasoline) (vapor) | 800–2000 nm | 10–20 cm | Quantitative |
| Organic, Carbon based Solvents (vapor) | 800–2000 nm | 10–20 cm | Quantitative |

First and second detection fibers 32, 42 extend through bulk head 49 and connector 48 to exit probe 12 through first and second output cables 25, 27 respectively. Output cables 25, 27 are also made of fiber optics, and are connected to spectrometer 18.

Figure 2B:
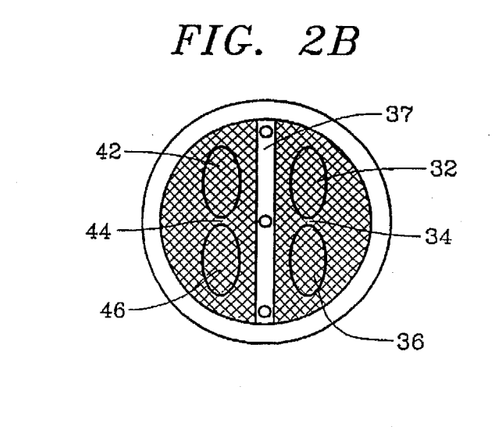
FIG. 2B is a plan view of the probe.

A screen 35 surrounds first and second emission fibers 36, 46 and first and second detection fibers 32, 42. This screen 35 prevents debris from entering first and second gaps 34, 44 and disrupting the light path between the respective emission and detection fibers. In addition, a wall 37, shown in side view in FIG. 2A and in top view in FIG. 2B, is placed between the respective pairs of emission and detection fibers 36, 32 and 46, 42. This wall 37 prevents stray light from one of the emission fibers 36, 46 from being diffracted into the other pair's detectors 42, 32 and thereby affecting the light signal detected across respective first and second gaps 34, 44.

Figure 3:
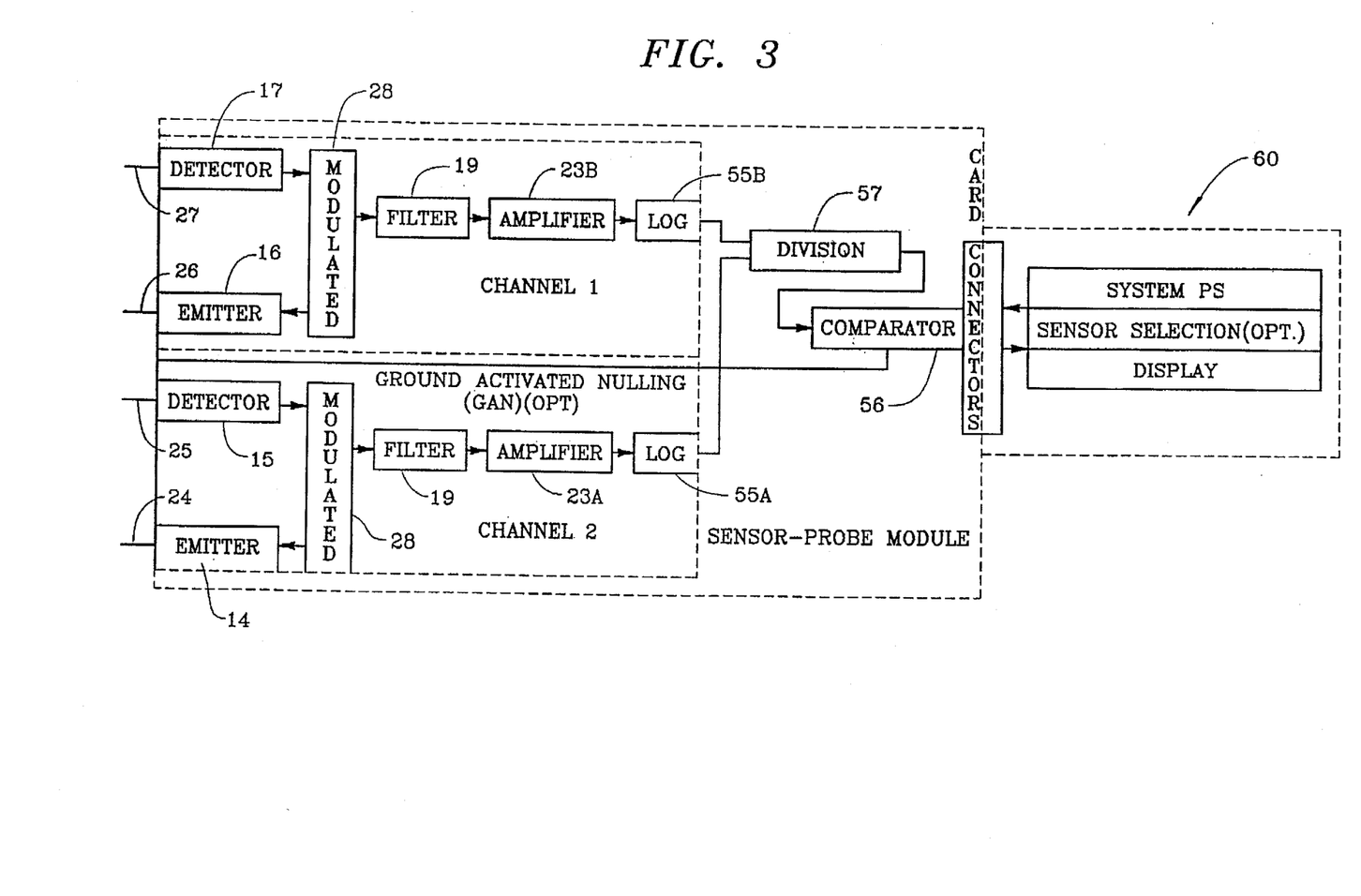
FIG. 3 is a block diagram of the electronics of the invention.

Spectrometer 18 comprises detectors 15, 17 and analyzes the absolute strength or intensity of the light received from first and second detection fibers 32, 34 which has been passed on to spectrometer 18 through first and second output cables 25, 27. Spectrometer 18 determines this absolute light strength for each frequency of light received from the respective first and second detection fibers 32, 34. In essence, spectrometer—light signals of varying amplitude into a proportional electric signal of varying electrical amplitude. Cadmium sulfide (CdS) or Lead Sulfide/Lead Selenium (PbS/PbSe) detectors 15, 17 have been found to be particularly adapted to perform this conversion.

Because two wavelengths of light are passed through the fluid to be tested, and because the light of different frequencies interact with the fluid differently, it is desirable to avoid having light at one wavelength scattered through the fluid into the detector corresponding to the other wavelength. This unwanted scattering is avoided by alternately "pulsing" or activating the respective light emitters 14, 16 and simultaneously activating the corresponding detectors 15, 17 within spectrometer 18. This "pulsing" is done by modulator 28 which is a timer connected to a switch which alternately activates and deactivates the respective light emitters 14, 16 and corresponding detectors 15, 17. An RCA-LM555CN timer and GE-CD4066 Quad-Bilateral Switch have been found to produce an excellent modulator 28. In this way, any scattered light of one wavelength which may be received by the other wavelength's fiber optic cables due to scattering through the fluid, impinges on an inactive detector. Because the detectors 15, 17 is inactivated by modulator 28, no "false" reading for the non-activated wavelength is created. Additionally, the "pulsing" or modulation of the emitters and detectors helps eliminate noise and drift, whether electronically or environmentally induced, which has been found to be present in long term, precision measurements.

After electrical signals corresponding in strength to the light received by respective first and second detection fibers 32, 34 has been determined, the analog voltage signal produced by each detector is filtered through filter 19 to improve the signal quality. Filter 19 may be any analog or digital voltage filter which suppresses spurious noise in the voltage signal from the detectors. For example, filter 19 may include an A to D converter followed by a digital filter followed in turn by a D to A converter. As another example, filter 19 may include a phase locked loop. Such filters are well known in the art. The resulting filtered signal is now a "clean" signal free of spurious noise.

This "clean" signal may be amplified by amplifiers 23 A, B to produce an appropriate signal strength as needed. The amplifiers 23 may be standard OP-AMPs. The outputs of amplifiers 23, A, B are passed to Log converters 55A, B which determine the Log of each wavelength's signal strength. Log converters 55A, B are diode feedback type Log converters or Log/Antilog Amps such as GE-1CL8048 which are well known in the art.

The outputs from Log converters 55A, B are then divided by Analog Divider 57 to produce a voltage based on the ratio of the outputs of amplifiers 23A, B. This voltage is indicative of the fluid quality. Analog divider 57 may be an analog divider/Multiplier such as the Burr-Brown MPY100AG. This establishes the ratio of the determined Logs according to the formula:

$$\text{Ratio} = \frac{\text{Log (Signal Strength of Wavelength 1)}}{\text{Log (Signal Strength of Wavelength 2)}}.$$

In another embodiment, a central processing unit may be appropriately connected to the outputs of amplifiers 23A, B to calculate, according to preprogrammed instructions, the ratio of voltages and produce a voltage or digital signal indicative of the ratio.

In the preferred embodiment, and in the alternate embodiment where a voltage representative of the ratio is produced, when the ratio and consequently voltage moves outside of preselected values, control signals are generated. The determination that the ratio is outside the preselected values is done by a comparator stage generally labeled 56. Comparator 56 may be a dual OPAMP or part of as standard Quad OP AMP configured to operate in a window.

In the alternate embodiment containing a central processing unit, the determination that the ratio is outside of the preselected values and the generation of control signals may be done by the central processing unit in response to preprogrammed instructions.

Figure 4:
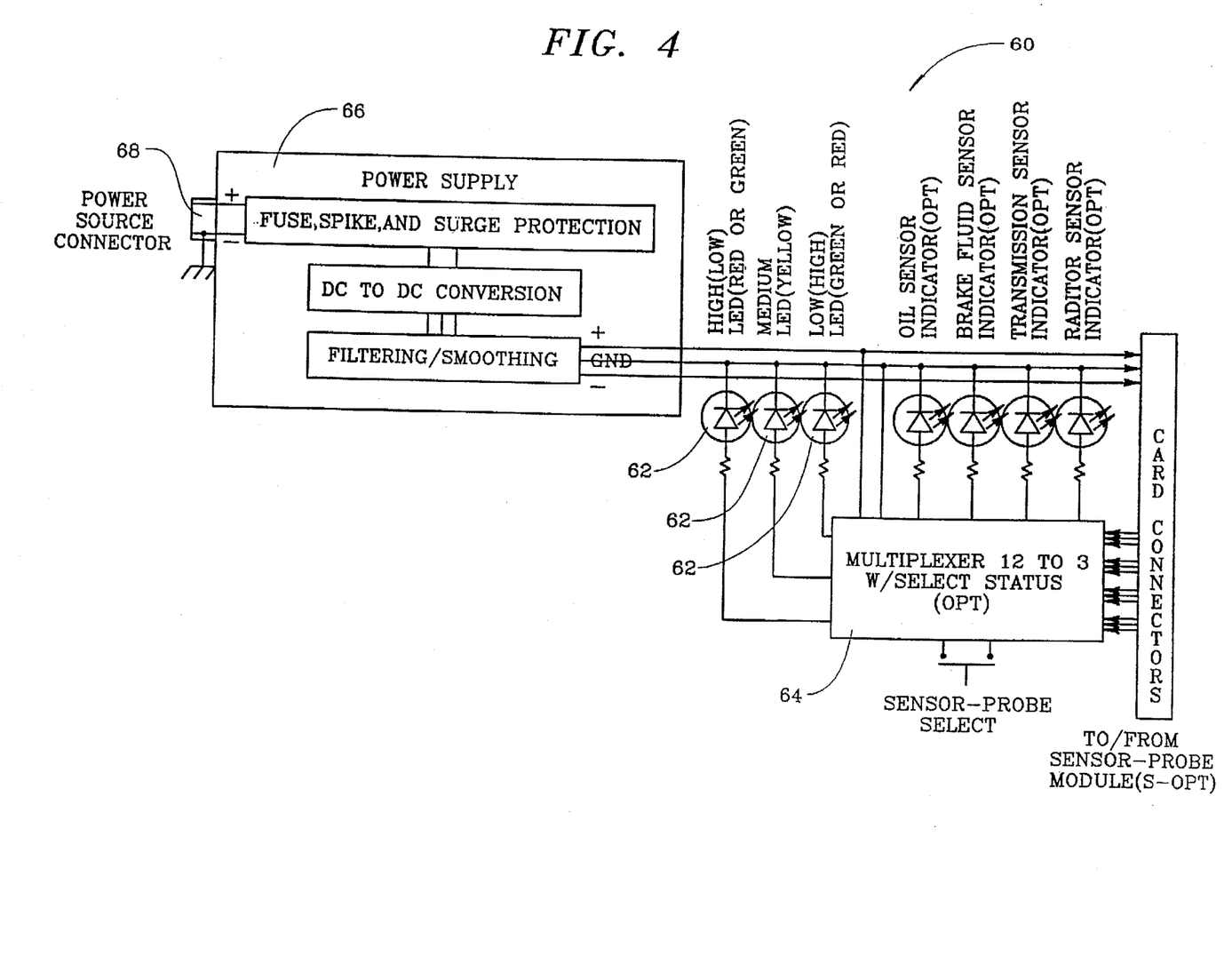
FIG. 4 is a block diagram of the preferred embodiment of the signaling system.

These control signals in turn activate signaling means 60 for alerting the operator that the fluid has moved outside the range of acceptable operating parameters. These signaling means 60 include, in the preferred embodiment (FIG. 4), LED's 62, activated through a multiplexer 64 connected to comparator 56, which visually indicate that the fluid is outside the acceptable operating parameters. Alternatively, or in addition, an audio alarm, or additional visual alarm means such as flashing lights, as well as the possibility of interacting with a computerized control system may also be used.

In the preferred embodiment, bulk head 49 also includes threads 39 which allow probe 12 to be inserted into the wall of a container containing a reservoir of the fluid or vapor to be tested. O-ring 38 is seated in bulk head 49 so that probe 12 will be in sealing contact with the wall of the container containing the fluid or vapor to be tested. Fiber optic input cables 24, 26 from the light sources 14, 16 themselves may then be attached to the appropriate fiber optic cables of the probe 12, or the light sources 14, 16 may themselves be attached to the ends of fiber optic cables of the probe 12.

Also in the preferred embodiment, a power supply 66 (FIG. 4) is provided which is connected to an alternating current source 68 such as a wall socket. Power supply 66 converts alternating current to direct current for powering the electronic components of the device 10 by means well known in the art.

In an alternate embodiment, a handle may be attached to bulkhead 49 to allow for manual placement of the probe 12 directly into a fluid or vapor to be tested. This embodiment of the invention will be particularly suited for testing samples of fluid in a spotcheck fashion. In this embodiment, the spectrometer 18, filter 19, log converters 55, comparator 56, analog divider 57 and signaling means 60, as well as first and second light source 14, 16 may all be contained in a single portable unit which is connected to probe 12 by first and second input and output cables 24, 26 and 25, 27, respectively. In this embodiment, power supply 66 is preferably a battery to render the device 10 more portable. However, the power supply of the preferred embodiment may also be used in this embodiment.

In the following examples, an analyte is present in a matrix. The invention detects the analyte in the minimum concentrations listed in the Tables corresponding to each example. The Tables also list the corresponding percentage of the analyte to the matrix. The Tables also list the preferred wavelengths of the first and second light sources for each matrix. Where the analyte is described as being gases or vapors, the gases or vapors are any gas or vapor including but not limited to ambient air and hydrocarbon fuel vapors.

In the examples, the wavelengths given for the first and second light sources are the preferred wavelengths. Where a range of wavelengths is given, it is to be understood that the range given corresponds to a preferred range of wavelengths for the first and second light sources. In either case, wavelengths other than those described may be used with the invention. In particular, as will be clear to those skilled in the art, the optimum wavelengths for operation of the invention may vary from the wavelengths disclosed due to factors related to the condition of the analyte and the fluid or vapor to be detected. Consequently, it may be desirable to vary the wavelengths of the first and second light sources from the values disclosed to obtain optimum detection of the fluid or vapor under the particular condition of the fluid or vapor and the analyte.

The wavelength of the first and second light sources may be varied by filtering the light output of the light sources or by shifting the electronic parameters of the light sources. For example, varying the voltage, current or temperature of the light sources will affect the wavelength of light emitted by the light sources.

Further, in the examples below, the gap length of gaps 34, 44 for the examples below are preferably about 1–20 mm for fluids and about 10–20 cm for gases or vapors. Once again, these values are given as the preferable values for the gap lengths. Due to the considerable variation in optical characteristics of the varied fluids, gases and vapors, optimal gap lengths are best determined by varying the gap length, preferably within the ranges given above, while the gaps 34, 44 are in place within the analyte and the device 10 is in operation.

EXAMPLE 1

Analyte: Water

Water is detected in the matrixes listed in Table 2.

TABLE 2

| Matrix | (ppm) | Limit (%) | Wavelengths (nm) #1/#2 |
|---|---|---|---|
| Transmission Fluid (Ex.: lubricating hydrocarbons, C18 to C80) | 50 | 0.005 | 960/700 |
| Gasoline (Ex.: octanes) | 45 | 0.0045 | 960/400 |
| Ethylene Glycol (Ex.: ethanol and alcohol) | 150 | 0.0150 | 960/400 |
| Antifreeze (mix) (Ex.: Standard consumer and commercial grades) | 3000 | 0.30 | 960/400 |
| Alcohol (Ex.: Commercial and consumer grades) | 50 | 0.005 | 970/400 |
| Dry Gas Streams (Ex.: Commercial and consumer gases containing less than 1 ppm of water) | 40 | 0.004 | 1440/1800 |
| Ambient Air (Ex.: Random air sample-any/all standard environments) | 75 | 0.0075 | 1400/1800 |
| Creams (Face, etc.- Beauty/cosmetic, containing emulsifiers, lipids, collagens, fragrances, surfactants, preservatives, etc.) | 100 | 0.010 | 1440/2000 |

EXAMPLE 2

Analyte: Protein

Protein, such as amide bonds and CO—N—H, is detected in the matrixes listed in Table 3.

TABLE 3

| Matrix | (ppm) | Limit (%) | Wavelengths (nm) #1/#2 |
|---|---|---|---|
| Water | 75 | 0.010 | 2180/600 |
| Urine | 250 | 0.025 | 2180/600 |
| Dietary Drinks | 300 | 0.030 | 2180/2100 |
| Milk | 100 | 0.010 | 2180/2100 |

EXAMPLE 3

Analyte: Fat

Fat, such as ester linkages, combinations and overtones, is detected in the matrixes listed in Table 4.

TABLE 4

| Matrix | (ppm) | Limit (%) | Wavelengths (nm) #1/#2 |
|---|---|---|---|
| Urine | 100 | 0.010 | 1734/600 |
| Milk | 150 | 0.015 | 1734/600 |
| Dietary Drinks | 150 | 0.015 | 1734/600 |

EXAMPLE 4

Analyte: Detergent

Detergent is detected in the matrixes listed in Table 5.

TABLE 5

| Matrix | (ppm) | Limit (%) | Wavelengths (nm) #1/#2 |
|---|---|---|---|
| Liquid Soaps (Ex.: consumer and commercial including sulphate bonds) | 100 | 0.010 | 1734/600 |

EXAMPLE 5

Analyte: Sugar

Sugar, including sugars having OH bonds, is detected in the matrixes listed in Table 6.

TABLE 6

| Matrix | (ppm) | Limit (%) | Wavelengths (nm) #1/#2 |
|---|---|---|---|
| Water | 100 | 0.010 | 2100/1600 |
| Urine | 150 | 0.015 | 2100/500 |
| Syrup | 200 | 0.020 | 2100/1700 |
| Fruit Juices | 150 | 0.015 | 2100/1700 |
| Soft Drinks | 125 | 0.013 | 2100/1970 |

EXAMPLE 6

Analyte: Artificial Sweetener

Artificial sweeteners, including saccarin, are detected in the matrixes listed in Table 7.

TABLE 7

| Matrix | (ppm) | Limit (%) | Wavelengths (nm) #1/#2 |
|---|---|---|---|
| Soft Drinks | 75 | 0.0075 | 224/600 |
| Iced Tea | 100 | 0.0100 | 224/600 |

EXAMPLE 7

Analyte: Colorants

Colorants are detected in the matrixes listed in Table 8.

TABLE 8

| Matrix | (ppm) | Limit (%) | Wavelengths (nm) #1/#2 |
|---|---|---|---|
| Paint | 100 | 0.010 | 2180/600 |
| Drinks | 50 | 0.005 | 2180/600 |
| Food colors | 50 | 0.005 | 400–700/900 |
| Aqueous Solutions | 75 | 0.0075 | 400–700/900 |

EXAMPLE 8

Analyte: Organic Preservatives

Organic preservatives, such as benzoates, parabens and ascorbic acids, are detected in the matrixes listed in Table 9.

TABLE 9

| Matrix | (ppm) | Limit (%) | Wavelengths (nm) #1/#2 |
|---|---|---|---|
| Soft drinks | 50 | 0.005 | 235/600 |
| Pharmaceutical | 75 | 0.0075 | 235/600 |
| Fruit Juice | 125 | 0.0125 | 235/600 |

EXAMPLE 9

Analyte: Salt

Salt is detected in the matrixes listed in Table 10.

TABLE 10

| Matrix | (ppm) | Limit (%) | Wavelengths (nm) #1/#2 |
|---|---|---|---|
| Urine | 250 | 0.025 | 1440/1460 |

EXAMPLE 10

Analyte: Alcohol

Alcohol, such as ethanol and methanol, is detected in the matrixes listed in Table 11.

TABLE 11

| Matrix | (ppm) | Limit (%) | Wavelengths (nm) #1/#2 |
|---|---|---|---|
| Water | 75 | 0.0075 | 2310/1440 |
| Beer | 100 | 0.0100 | 2310/1440 |
| Wine | 90 | 0.0090 | 2310/1440 |
| Whiskey | 90 | 0.0090 | 2310/1440 |
| Fermentation Broth | 150 | 0.0150 | 2310/1440 |
| Pharmaceutical Mix | 125 | 0.0125 | 2310/1440 |
| Mouthwash | 100 | 0.0100 | 2310/1440 |
| Gasoline | 230 | 0.0230 | 1450/1000 |

EXAMPLE 11

Analyte: Nutrients

Nutrients, such as proteins and starches, are detected in the matrixes listed in Table 12.

TABLE 12

| Matrix | (ppm) | Limit (%) | Wavelengths (nm) #1/#2 |
|---|---|---|---|
| Fermentation Broth | 250 | 0.025 | 2055–2180/600 |

EXAMPLE 12

Analyte: Particulates

Light scattering particulates, such as $TiO_2$, are detected in the matrixes listed in Table 13.

TABLE 13

| Matrix | (ppm) | Limit (%) | Wavelengths (nm) #1/#2 |
|---|---|---|---|
| Solutions | 50 | 0.0050 | 300/800 |
| Paints | 50 | 0.0050 | 300/800 |
| Suspensions | 50 | 0.0050 | 300/800 |

EXAMPLE 13

Analyte: Bacterial Growth

Light scattering bacterial growths, such as *E-coli*, are detected in the matrixes listed in Table 14.

TABLE 14

| Matrix | (ppm) | Limit (%) | Wavelengths (nm) #1/#2 |
|---|---|---|---|
| Sterile Solutions | 50 | 0.0050 | 300/800 |
| Fruit Drinks | 75 | 0.0075 | 300/800 |

EXAMPLE 14

Analyte: Adulterants

Adulterants, such as denaturants and organic trace materials, are detected in the matrix listed in Table 15.

TABLE 15

| Matrix | (ppm) | Limit (%) | Wavelengths (nm) #1/#2 |
|---|---|---|---|
| Alcohol (Ex.: benzene and SD 30 and 40 alcohols) | 75 | 0.0075 | 3100–3600/ 2500 |
| Water | 75 | 0.0075 | 3100–3600/ 2500 |

EXAMPLE 15

Analyte: Aromatics

Aromatics, such as polyaromatic hydrocarbons and benzene, are detected in the matrix listed in Table 16.

TABLE 16

| Matrix | (ppm) | Limit (%) | Wavelengths (nm) #1/#2 |
|---|---|---|---|
| Gasoline | 75 | 0.0075 | 300/800 |

EXAMPLE 16

Analyte: Carbon Dioxide

Carbon dioxide is detected in the matrixes listed in Table 17.

TABLE 17

| Matrix | (ppm) | Limit (%) | Wavelengths (nm) #1/#2 |
|---|---|---|---|
| Soft Drinks | 200 | 0.020 | 4250/1440 |
| Dry Gases | 50 | 0.005 | 4250/600 |
| Exhaled Breath | 100 | 0.010 | 4250/600 |

EXAMPLE 17

Analyte: CO bonds

CO (carbon monoxide) is detected in the matrix listed in Table 18.

TABLE 18

| Matrix | (ppm) | Limit (%) | Wavelengths (nm) #1/#2 |
|---|---|---|---|
| Dry gases | 50 | 0.005 | 4250/600 |
| Exhaled Breath | 100 | 0.010 | 4250/600 |

EXAMPLE 18

Analyte: Fuel Vapors

Fuel vapors, such as C—H bonds, Methylene ($CH_2$) and Methyl ($CH_3$), are detected in the matrixes listed in Table 19.

TABLE 19

| Matrix | (ppm) | Limit (%) | Wavelenghts (nm) #1/#2 |
|---|---|---|---|
| Open storage tanks | 50 | 0.005 | 3400/600 |
| Closed storage tanks | 20 | 0.002 | 3400/600 |

EXAMPLE 19

Analyte: Anesthesia Gases

Anesthesia gases are detected in the matrix listed in Table 20.

TABLE 20

| Matrix | (ppm) | Limit (%) | Wavelengths (nm) #1/#2 |
|---|---|---|---|
| Halothane | 25 | 0.0025 | 600/ 1150–2000 |
| Iso Fluorane | 25 | 0.0025 | 600/ 1150–2000 |
| N Fluorane | 25 | 0.0025 | 600/ 1150–2000 |

EXAMPLE 20

Analyte: Dopant Mix

Dopant mixes, such as $PH_3$ and $B_2H_6$, are detected in gases and vapors according to the parameters listed in Table 21.

TABLE 21

| Analyte | (ppm) | Limit (%) | Wavelengths (nm) #1/#2 |
|---|---|---|---|
| $PH_3$ | 100 | 0.010 | 4100–4400/600 |
| $B_2H_6$ | 100 | 0.010 | 2700–4000/600 |

EXAMPLE 21

Analyte: Carbon Based Gases

Carbon based gases, such as CO (Carbon Monoxide) and $CO_2$ (Carbon Dioxide), are detected in gases or vapors according to the parameters listed in Table 22.

TABLE 22

| Analyte | (ppm) | Limit (%) | Wavelengths (nm) #1/#2 |
|---|---|---|---|
| CO | 50 | 0.0050 | 2900–4500/600 |
| $CO_2$ | 50 | 0.0050 | 2900–4000/600 |

EXAMPLE 22

Analyte: Silicon Precursors

Silicon precursors, such as $SiH_4$, $SiH_2Cl_2$ and $SiClH_3$, are detected in gases and vapors according to the parameters listed in Table 23.

TABLE 23

| Analyte | (ppm) | Limit (%) | Wavelengths (nm) #1/#2 |
|---|---|---|---|
| $SiH_4$ | 100 | 0.010 | 4400–4760/600 |
| $SiH_2Cl_2$ | 100 | 0.010 | 4400–4760/600 |
| $SiClH_3$ | 100 | 0.010 | 4400–4760/600 |

The invention has been described primarily in relation to fluids. However, it works equally well when addressed to the analysis of vapors. When used in this context, vapors instead of fluid is present in the gap 34, 44 between the fiber optic cables.

While the invention has been described in what is considered to be the preferred embodiment, as well as alternative embodiments, it is to be understood that these descriptions are given by means of example only, and not by means of limitation. It is to be understood that changes and modifications may be made to the description given and still be within the scope of the invention. Further, it is clear that obvious changes and modifications will occur to those skilled in the art.

What I claim is:

1. A non-destructive diagnostic device for continuously testing fluid, gas or vapor contained in a fluid, gas or vapor reservoir comprising:

a) at least two light sources, each of said light sources emitting light at a different preselected wavelength, each of said light sources directing light into the fluid, gas or vapor reservoir;

b) detectors for receiving light from each of said light sources after it has been directed through the reservoir, said detectors positioned a distance from said light sources thereby forming a gap through which the fluid or vapor may pass;

c) means, connected to said detectors, for determining the absolute intensity of light from each of said light sources after the light has been directed through the fluid, gas or vapor in the reservoir and detected by said detectors;

d) means for determining the ratio of absolute intensity of light detected by each of said detectors after the light has been directed through the fluid, gas or vapor; and, e) means, responsive to said means for determining, for creating a control signal indicating that said ratio is outside of a preselected limit.

2. The device of claim 1, wherein said light sources are chosen from a group consisting of photodiodes, light emitting diodes, laser diodes, SRLEDs, lasers, and monochromatic incandescent light bulbs.

3. The device of claim 1, wherein said light sources include a filter placed between said source of light and said reservoir, said filter passing light of said preselected wavelength to said reservoir.

4. The device of claim 1 further comprising input fiber optic cables having a first end positioned to receive light emitted from said light sources and a second end in the reservoir to pass light from said light sources to said reservoir.

5. The device of claim 1 further comprising output fiber optic cables and input fiber optic cables, each of said output fiber optic cables having a first end positioned in the reservoir and a second end positioned to receive light from one of said light sources, each of said input fiber optic cables having a first end positioned in the reservoir spaced from one of said first ends of said output fiber optic cables to form said gap, each of said input fiber optic cables having a second end positioned to transmit light to said detectors.

6. The device of claim 1 further comprising a probe, said probe being insertable into said fluid or vapor to be tested, said probe including fiber optic input cables connecting each of said light sources with said fluid or vapor to be tested, said probe also including fiber optic output cables connecting said fluid or vapor to be tested to said detectors, said input and output cables extending into and out of, respectively, said probe, said input and output cables corresponding to each of said light sources being separated from each other within said probe thereby forming said gap, each of said gaps in contact with said fluid or vapor whereby fluid or vapor to be tested may move through each of said gaps between said input and output cables so that light from said each of said respective light sources travels through said input cables, through said gap, and through said output cables before impinging on said detectors.

7. The device of claim 1, wherein said detectors comprises a spectrometer.

8. The device of claim 1, wherein said means for determining the ratio of absolute intensity of light comprises an analog divider.

9. The device of claim 1, wherein said means for creating control signals includes a central processing unit electronically connected to said means for determining the ratio of absolute intensity of light and programmable to generate a control signal when said ratio of absolute intensity of light is determined by said means for determining the ratio to be outside of a range of operating parameters preprogrammed into said central processing unit.

10. The device of claim 1 further comprising means for modulating said light sources.

11. The device of claim 1, further comprising means for communicating said control signal.

12. The device of claim 11 wherein said means for communicating is chosen from a group consisting of light emitting diodes, sirens, whistles, incandescent lights, bells, and digital logical electrical signals.

13. A non-destructive diagnostic device for continuously testing, gases or vapors contained in a reservoir for carbon based gases, comprising:

a) at least two light sources, each of said light sources emitting light at a different preselected wavelength, each of said light sources directing light through the gas or vapor;

b) detectors for receiving light from each of said light sources after it has been directed through the gas or vapor in the reservoir, said detectors positioned a distance from said light sources thereby forming a gap through which the gas or vapor may pass;

c) means for determining the absolute intensity of the light of the different wavelengths after the light has been detected;

d) means for determining the ratio of the determined absolute intensities of the light; and, e) means for comparing the determined ratio to a preestablished ratio of absolute intensities of light to determine whether the determined ratio indicates that the condition of the sample is outside acceptable values.

14. The device of claim 13 wherein the carbon based gas is carbon monoxide and first wavelength of said light sources is between 2900 and 4500 nanometers and the second wavelength of said light sources is about 600 nanometers.

15. The device of claim 13 wherein the carbon based gas is carbon dioxide and first wavelength of said light sources is between 2900 and 4000 nanometers and the second wavelength of said light sources is about 600 nanometers.

16. A method for non-destructively and continuously testing a gas or vapor matrix for the presence of an analyte, the gas or vapor contained in a gas or vapor reservoir, the analyte being a carbon based gas taken from a group consisting of carbon monoxide or carbon dioxide, the method comprising the steps of:

a) passing light of at least two different wavelengths through the reservoir of gases or vapors;

b) detecting the light of the different wavelengths after the light has passed through the reservoir;

c) determining the absolute intensity of the light of the different wavelengths after the light has been detected;

d) determining the ratio of the determined absolute intensities of the light; and, e) comparing the determined ratio to a preestablished ratio of absolute intensities of the light to determine whether the determined ratio indicates that the analyte is present in the gas or vapor.

* * * * *